United States Patent [19]

Schott et al.

[11] 4,447,255

[45] May 8, 1984

[54] PLANT GROWTH REGULATORS

[75] Inventors: Eberhard P. Schott, Neustadt; Hans Lang, Limburgerhof, both of Fed. Rep. of Germany

[73] Assignee: BASF Aktiengesellschaft, Fed. Rep. of Germany

[21] Appl. No.: 965,263

[22] Filed: Dec. 1, 1978

[30] Foreign Application Priority Data

Dec. 15, 1977 [DE] Fed. Rep. of Germany ..... 27559406

[51] Int. Cl.³ ............................................. A01N 57/12
[52] U.S. Cl. .......................................... 71/86; 71/94; 71/95
[58] Field of Search ..................................... 71/86, 94

[56] References Cited

PUBLICATIONS

British Farmer and Stockbreeder, "Breakthrough with Barley", Mar. 18, 1978.
Arable Farming, "Barley Growth Regulator Eliminates Ear Losses", Jan. 1979.
Arable Farming, "Sorting Out Seed Rates and Topdressings," Jan. 1979.
Irish Farmers' Journal, "Terpal Works," Jul. 14, 1979.
The Scottish Farmer, "Boost in Spring Barley Margins Expected," Dec. 8, 1979.
Terpal Leaflet–Chemical, Physical and Biological Properties, (23 pp.), (BASF) Mar. 1979.
Ratschläge für den Getreidebav, BASF (1980) pp. 2 and 3.

*Primary Examiner*—Catherine L. Mills
*Attorney, Agent, or Firm*—Keil & Witherspoon

[57] ABSTRACT

New agents for regulating plant growth, especially for reducing the height of plants, containing a mixture of a quaternary substituted thianium or ammonium salt and a phosphonic acid derivative.

2 Claims, No Drawings

PLANT GROWTH REGULATORS

The present invention relates to agents for regulating plant growth which contain a mixture of active ingredients, and to processes for regulating plant growth with these agents.

It has been disclosed to use quaternary ammonium compounds, e.g., N,N-dimethylpiperidinium salts (German Laid-Open Application DE-OS No. 2,207,575), and phosphonic acid derivatives, e.g., 2-chloroethanephosphonic acid (German Printed Application DE-AS No. 1,667,968) for regulating plant growth. It has also been disclosed to use mixtures of N,N,N-trimethyl-N-2-chloroethylammonium chloride and 2-chloroethanephosphonic acid for regulating plant growth (German Laid-Open Application DE-OS No. 2,361,410). It has further been disclosed to use salts, e.g., the N,N-dimethylpiperidinium salt of 2-chloroethanephosphonic acid, for regulating plant growth (German Laid-Open Application DE-OS No. 2,422,807).

We have now found that mixtures of (a) a quaternary substituted thianium or ammonium salt selected from the group consisting of
N,N-dimethylazacycloheptanium salts,
N,N-dimethylpiperidinium salts,
N,N-dimethylhexahydropyridazinium salts,
N,N-dimethyltetrahydropyridazinium salts,
N-methylpyridazinium salts,
N,N-dimethylpyrrolidinium salts, and
S-methylthiacyclohexanium salts and (b) a phosphonic acid derivative selected from the group consisting of
2-chloroethylphosphonic acid,
2-chloroethylaminoethylphosphonic acid,
2-chloroethylaminobutylphosphonic acid,
2-chloroethylphosphonic acid-N,N-dimethylamide,
2-chloroethylphosphonic acid-N,N-methylamide,
vinylphosphonic acid,
propylphosphonic acid,
phosphonomethylglycine,
bis-phosphonomethylglycine, and
benzylphosphonic acid are eminently suitable for regulating plant growth.

Examples of particularly suitable salts are the halides (chlorides, bromides), and especially the chlorides.

Regulation of plant growth may include for instance the following plant responses:

Inhibition of cell elongation, e.g., reduction in stem height and internodal distance, strengthening of the stem wall, thus increasing the resistance to lodging, which is a precondition for ensuring yields in cereals and other Gramineae for corn or seed production, and in fiber plants from which textile fibers are obtained:

compact growth in ornamentals for the economic production of improved quality plants;

promotion of better fruiting, e.g., increased fruit set in pomes, drupes and aggregate fruit, grapes, citrus fruits, almonds, olives, cacao, and coffee plants;

increase in number of ovaries with a view to stepping up yield, e.g., in Cucurbitaceae and papaya;

promotion of senescence or the formation of tissue enabling fruit to absciss, e.g., improvement in fruit drop for facilitating the mechanical harvesting of citrus fruits, drupes, pomes and aggregate fruit, olives, almonds, coffee and indehiscent fruit;

defoliation of nursery and ornamental bushes and trees for mail-order business in the fall;

defoliation of trees to interrupt parasitic chains of infection, e.g., *Gloeosporium heveae* in *Heva brasiliensis;* hastening of ripening, e.g., in tomatoes, citrus fruits, pineapples and coffee, with a view to programming the harvest and promoting fruit color, or, in cotton, reducing the harvest to 1 to 2 pickings and interrupting the food-chain for injurious insects.

The new mixtures have a synergistic action particularly in cereals, i.e., the action of the mixture is better than the sum of the actions of the individual active ingredients. The new compositions are also better tolerated than prior art compounds and result in improved rigor in cereals—a decrease in lodging is observed.

Particularly the mixtures of N,N-dimethylpiperidinium chloride or N,N-dimethylhexahydropyridazinium bromide with 2-chloroethanephosphonic acid, 2-chloroethyl-O-(2'-aminoethyl)-phosphonic acid, 2-chloroethylphosphonic acid-N,N-dimethylamide or 2-chloroethyl-O-(2'-amino-n-butyl)-phosphonic acid have a good growth-regulating action.

The ratio of the active ingredients to each other may vary within wide limits, e.g., 10:1 to 1:10 parts by weight, especially 4:1 to 1:4, and preferably 3:1 to 1.3:1.

The agents according to the invention may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be parepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions oils of various types, wetting agents or adherents, herbicides, fungicides, nematocides, insecticides, bactericides, trace elements, fertilizers, synergists, antifoams (e.g., silicones), growth regulators, and antidotes.

The following examples of field experiments confirm the superior biological action of the compositions over their individual components.

The mixtures are preferably used in the form of aqueous solutions. The mixtures are applied in conventional manner, e.g., by spraying, atomizing, watering or disinfecting seed.

EXAMPLE 1

Spring barley, "Villa" variety

Treatment was effected with aqueous solutions of the active ingredients 74 days after sowing. 101 days after sowing, the height of the plants was measured (average from 100 measurements).

The resistance of the plants to lodging was assessed 124 days after sowing, 1 denoting best resistance, graduated down to 9 denoting no resistance to lodging.

| Active ingredient | Appln. rate g/ha | Growth height cm | Reduction in growth height cm | Resistance to lodging | Improvement in resistance to lodging over control |
|---|---|---|---|---|---|
| Untreated (control) | — | 85.5 | — | 3.5 | — |
| DPC | 920 | 83.4 | 2.1 | 2.5 | 1.0 |
| CEPA | 442 | 80.8 | 4.7 | 2.5 | 1.0 |
| DPC + CEPA | 920 + 442 | 77.4 | 8.1 | 1.0 | 2.5 |
| DPC + | 920 + | 76.4 | 9.1 | | |

| Active ingredient | Appln. rate g/ha | Growth height cm | Reduction in growth height cm | Resistance to lodging | Improvement in resistance to lodging over control |
|---|---|---|---|---|---|
| CEPA | 884 | | | | |

DPC = N,N—dimethylpiperidinium chloride
CEPA = 2-chloroethylphosphonic acid

These results demonstrate, with regard to the reduction in height, the synergistic action of the composition compared with its components.

EXAMPLE 2

Winter barley, "Birgit" variety

Treatment was effected with aqueous solution of the active ingredients 219 days after sowing. Harvesting took place 281 days after sowing.

| Active ingredient | Appln. rate g/ha | Grain yield decitonnes/ha | 100% |
|---|---|---|---|
| Untreated | — | 72.4 | 100 |
| DPC | 920 | 72.5 | 100 |
| CEPA | 442 | 78.3 | 108 |
| DPC + CEPA | 920 + 442 | 80.0 | 110 |

This example also demonstrates that the mixture results in a synergistic increase in yield compared with the individual components.

EXAMPLE 3

Oats, "Flamingskrone" variety

Treatment was effected with aqueous solutions of the active ingredients 72 days after sowing. The resistance to lodging was assessed 131 days after sowing.

| Active ingredient | Appln. rate g/h | Resistance to lodging | Improvement in resistance to lodging |
|---|---|---|---|
| Untreated | — | 7.0 | — |
| DPC | 460 | 6.7 | 0.3 |
| CEPA | 221 | 7.0 | 0 |
| DPC + CEPA | 460 + 221 | 6.3 | 0.7 |

Even when the untreated plants lodge fairly severely, the mixture results in a synergistic improvement in the resistance to lodging.

EXAMPLE 4

Oats, "Borrus" variety

Treatment was effected with aqueous solutions of the active ingredients 80 days after sowing. The height of the plants was measured 105 days after sowing. Harvesting was carried out 4 months after sowing.

| Active ingredient | Appln. rate g/ha | Growth height cm | Reduction in growth height cm | Grain yield decitonnes/ha | % |
|---|---|---|---|---|---|
| Untreated | — | 83.9 | — | 42.1 | 100 |

-continued

| Active ingredient | Appln. rate g/ha | Growth height cm | Reduction in growth height cm | Grain yield decitonnes/ ha | % |
|---|---|---|---|---|---|
| DPC | 460 | 83.9 | 0 | 38.3 | 91 |
| CEPA | 221 | 83.4 | 0.5 | 38.1 | 90 |
| DPC + CEPA | 460 + 221 | 83.1 | 0.8 | 45.2 | 107 |
| DPC + CEPA | 460 + 442 | 83.0 | 0.9 | 40.8 | 97 |

These results clearly show the synergistic action of the mixtures compared with their components.

EXAMPLE 5

Winter rye, "Carokurz" variety

Treatment was effected with aqueous solutions of the active ingredients 196 days after sowing. The height of the plants was measured 235 days after sowing.

| Active ingredient | Appln. rate g/ha | Growth height cm | Reduction in growth height cm |
|---|---|---|---|
| Untreated | — | 142.7 | — |
| DPC | 460 | 140.2 | 2.5 |
| CEPA | 221 | 141.0 | 1.7 |
| DPC + CEPA | 460 + 221 | 134.5 | 8.2 |

As in the other cereal species, the mixture resulted in a synergistic reduction in growth height here too.

EXAMPLE 6

Winter rye, "Kustro" variety

Treatment was effected with aqueous solutions of the active ingredients 209 days after sowing. Harvesting was carried out 282 days after sowing.

| Active ingredient | Appln. rate g/ha | Grain yield decitonnes/ha | % |
|---|---|---|---|
| Untreated | — | 40.5 | 100 |
| DPC | 1,380 | 42.9 | 106 |
| CEPA | 1,440 | 38.6 | 95 |
| DPC + CEPA | 690 + 240 | 43.9 | 108 |

These results show that a mixture in an approximate ratio of 3:1 exercises a good influence on the grain yield.

EXAMPLE 7

Indian corn, "Limac" variety

Treatment was effected with aqueous solutions of the active ingredients 60 days after sowing. The height of the plant was measured 90 days after sowing. Harvesting was carried out 167 days after sowing.

| Active ingredient | Appln. rate g/ha | Growth height cm | Reduction in growth height cm | Cobs/m$^2$ no. | % |
|---|---|---|---|---|---|
| Untreated | — | 168.0 | — | 9.1 | 100 |
| DPC | 920 | 164.6 | 3.4 | 9.2 | 101 |
| CEPA | 721 | 136.1 | 31.9 | 8.9 | 98 |
| DPC + CEPA | 920 + 721 | 129.4 | 38.6 | 9.4 | 103 |

The mixture has a synergistic action compared with its components both with regard to the reduction in growth height and to the member of cobs formed. The usually undersirable growth of the plants is restricted in favor of an increase in yield.

EXAMPLE 8

Winter barley, "Mirra" variety

Treatment was effected with aqueous solutions of the active ingredients 200 days after sowing. The height of the plants was measured 227 days after sowing. The resistance to lodging was assessed 270 days after sowing.

| Active ingredient | Appln. rate g/ha | Growth height cm | Reduction in growth height cm | Resistance to lodging | Improvement |
|---|---|---|---|---|---|
| (1) Untreated | — | 94.0 | — | 6.5 | 0 |
| (2) N,N—dimethylhexahydropyridazinium bromide | 920 | 90.2 | 3.8 | 4.0 | 2.5 |
| (3) 2-chloroethyl-O—(2'-amino-n-butyl)-phosphonic acid | 960 | 89.3 | 4.7 | 4.5 | 2.0 |
| 2 + 3 | 920 + 480 | 78.0 | 16.0 | 1.5 | 5.0 |

The mixture has a synergistic action compared with its components both with regard to the reduction in growth height and improvement in the resistance to lodging.

EXAMPLE 9

Winter barley, "Ogra" variety

Treatment was effected with aqueous solutions of the active ingredients 213 days after sowing. The growth height was measured 232 days, and the resistance to lodging assessed 244 days after sowing. Harvesting was carried out 288 days after sowing.

| Active ingredient | Appln. rate g/ha | Growth height cm | Reduction in growth height cm | Resistance to lodging | Improvement in resistance to lodging | Grain yield decitonnes/ha | % |
|---|---|---|---|---|---|---|---|
| (1) Untreated | — | 129.0 | — | 4.0 | — | 58.1 | 100 |
| (2) DPC | 920 | 126.4 | 2.6 | 3.7 | 0.3 | 57.5 | 99 |
| (3) 2-chloroethyl-O—(2'-aminoethyl)-phosphonic acid | 480 | 127.7 | 1.3 | 2.7 | 1.3 | 59.5 | 102 |
| (4) 2 + 3 | 920 + 480 | 122.6 | 6.4 | 1.3 | 2.7 | 60.9 | 105 |

This mixture, too, exhibits synergism compared with its components. The growth height, resistance to lodging and the grain yield are significantly improved.

EXAMPLE 10

Winter barley, "Dura" variety

Treatment was effected with aqueous solutions of the active ingredients 124 days after sowing. Harvesting was carried out 185 days after sowing.

| Active ingredient | Appln. rate g/ha | Grain yield decitonnes/ha | % |
|---|---|---|---|
| (1) Untreated | — | 47.5 | 100 |
| (2) DPC | 920 | 51.4 | 108 |
| (3) 2-chloroethyl-phosphonic acid-N,N-dimethylamide | 240 | 49.1 | 103 |
| (4) 2 + 3 | 920 + 480 | 53.7 | 113 |

This example illustrates to what a considerable extent the yield can be increased with the mixture.

EXAMPLE 11

Spring rye, "Beacon" variety

Treatment was effected with aqueous solutions of the active ingredients 59 days after sowing. The height of the plants was measured 100 days after sowing.

| Active ingredient | Appln. rate g/ha | Growth height cm | Reduction in growth height cm |
|---|---|---|---|
| (1) Untreated | — | 66 | — |
| (2) DPC | 515 | 65 | 1 |
| (3) CEPA | 134 | 67 | −1 |
| (4) 2 + 3 | 515 + 134 | 62 | 4 |

This example demonstrates that a mixture of a ratio of 4:1 has a synergistic action compared with its components.

EXAMPLE 12

Winter rye, "Kustro" variety

Treatment was effected with aqueous solutions of the active ingredients 204 days after sowing. The height of the plants was measured 232 days after sowing, and harvesting was carried out 285 days after sowing.

| Active ingredient | Appln. rate g/ha | Growth height cm | Reduction in growth height cm | Grain yield decitonnes/ha | % |
|---|---|---|---|---|---|
| (1) Untreated | — | 154.2 | — | 55.70 | 100 |
| (2) A | 1,840 | 143.2 | 11.0 | 55.02 | 99 |
| (3) DPC + CEPA | 1,220 + 620 | 134.8 | 19.4 | 56.74 | 102 |

A = N,N—dimethylpiperidinium salt of 2-chloroethanephosphonic acid (disclosed in German Laid-Open Application DE-OS 2,422,807).

The reduction in growth height and the increased grain yield demonstrate the clearly superior action of mixture 3 over that of prior art salt A.

EXAMPLE 13

Winter rye, "Kustro" variety

Treatment was effected with aqueous solutions of the active ingredients 206 days after sowing. The resistance to lodging was assessed 261 days after sowing and harvesting was carried out 288 days after sowing.

| Active ingredient | Appln. rate g/ha | Resistance to lodging | Improvement in resistance to lodging | Grain yield decitonnes/ha | % |
|---|---|---|---|---|---|
| (1) Untreated | — | 6.8 | — | 53.1 | 100 |
| (2) A | 1,380 | 3.8 | 3.0 | 54.6 | 103 |
| (3) DPC + CEPA | 915 + 465 | 2.3 | 4.5 | 56.4 | 106 |

A = N,N—dimethylpiperidinium salt of 2-chloroethanephosphonic acid

Here, too, the mixture is clearly superior to the salt A both with regard to the improvement in resistance to lodging and increase in yield.

EXAMPLE 14

Spring rye, "Somro" variety

Treatment was effected with aqueous solutions of the active ingredients 85 days after sowing. The height of the plants was measured 100 days after sowing, and harvesting was carried out 153 days after sowing.

| Active ingredient | Appln. rate g/ha | Growth height cm | Reduction in growth height cm | Grain yield decitonnes/ha | % |
|---|---|---|---|---|---|
| (1) Untreated | — | 196.3 | — | 34.4 | 100 |
| (2) A | 920 | 184.9 | 11.4 | 34.0 | 99 |
| (3) DPC + CEPA | 610 + 310 | 183.4 | 12.9 | 36.1 | 105 |

A = N,N—dimethylpiperidinium salt of 2-chloroethanephosphonic acid

In spring rye, too, the action of the mixture is superior to that of salt A both with regard to the reduction in growth height and the increase in grain yield.

EXAMPLE 15

Winter barley, "Ago" variety

Treatment was effected with aqueous solutions of the active ingredients 208 days after sowing. The resistance to lodging was assessed 271 days after sowing, and harvesting was carried out 279 days after sowing.

| Active ingredient | Appln. rate g/ha | Resistance to lodging | Improvement in resistance to lodging | Grain yield decitonnes/ha | % |
|---|---|---|---|---|---|
| (1) Untreated | — | 7.5 | — | 58.6 | 100 |
| (2) A | 1,840 | 7.0 | 0.5 | 50.5 | 86 |
| (3) DPC + CEPA | 1,220 + 620 | 5.0 | 2.5 | 64.5 | 110 |

A = N,N—dimethylpiperidinium salt of 2-chloroethylphosphonic acid

Treatment with mixture 3 results, compared with treatment with salt A, in a considerably improved resistance to lodging, and, due to superior crop plant tolerance, a clear increase in yield.

EXAMPLE 16

Grass of the Phleum pratense, var. "Holea" variety

Treatment was effected with aqueous solutions of the active ingredients about 2 years after sowing. The resistance to lodging was assessed 90 days after treatment.

| Active ingredient | Appln. rate g/ha | Resistance to lodging(x) | Improvement in resistance to lodging |
|---|---|---|---|
| (1) Untreated | — | 4.2 | — |
| (2) N,N—dimethylhexahydro-pyridazinium bromide | 5,520 | 4.0 | 0.2 |
| (3) 2-chloroethyl-O—(2'-aminoethyl)-phosphonic acid | 17,280 | 3.8 | 0.4 |
| (4) 2 + 3 | 3,680 + 12,960 | 3.2 | 1.0 |

(x)1 = no lodging 9 = completely flat

EXAMPLE 17

Grass of the Festuca pratensis, var. "Cosmos 11" variety

Treatment was effected with aqueous solutions of the active ingredients 270 days after sowing. Harvesting was carried out 45 days after treatment.

| Active ingredient | Appln. rate g/ha | Seed yield kg/ha | % | Improvement in yield kg/ha |
|---|---|---|---|---|
| (1) Untreated | — | 306 | 100 | — |
| (2) N,N—dimethylhexahydropyridazinium bromide | 5,520 | 351 | 115 | 45 |
| (3) 2-chloroethyl-O—(2'-aminoethyl)-phosphonic acid | 17,280 | 375 | 123 | 69 |
| (4) 2 + 3 | 3,680 + 12,960 | 425 | 139 | 119 |

EXAMPLE 18

Grass of the Trisetum flavescens, var. "Trisett 51" variety

Treatment was effected with aqueous solutions of the active ingredients about 4 years after sowing. Harvesting was carried out 30 days after treatment.

| Active ingredient | Appln. rate g/ha | Seed yield kg/ha | % | Improvement in yield kg/ha |
|---|---|---|---|---|
| (1) Untreated | — | 224 | 100 | — |
| (2) N,N—dimethylhexa-hydropyridazinium bromide | 5,520 | 294 | 131 | 70 |
| (3) 2-chloroethyl-O—(2'-aminoethyl)-phosphonic acid | 17,280 | 229 | 102 | 5 |
| (4) 2 + 3 | 3,680+ 12,960 | 320 | 143 | 96 |

EXAMPLE 19

Grass of the Trisetum flavescens, "Trisett 51" variety

Treatment was effected with aqueous solutions of the active ingredients about 4 years after sowing. Harvesting was carried out 30 days after treatment.

| Active ingredient | Appln. rate g/ha | Seed yield kg/ha | % | Improvement in yield kg/ha |
|---|---|---|---|---|
| (1) Untreated | — | 224 | 100 | — |
| (2) DPC | 5,520 | 280 | 125 | 56 |
| (3) 2-chloroethyl-O—(2'-aminoethyl)-phosphonic acid | 17,280 | 229 | 102 | 5 |
| (4) 2 + 3 | 3,680+ 12,960 | 286 | 128 | 62 |

EXAMPLE 20

70 parts by weight of the mixture employed in Example 2 is mixed with 30 parts by weight of water. A solution is obtained which is suitable for application in the form of very fine drops.

EXAMPLE 21

20 parts by weight of the mixture employed in Example 3 is dissolved in a mixture consisting of 80 parts by weight of water, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 22

20 parts by weight of the mixture employed in Example 2 is dissolved in a mixture consisting of 70 parts by weight of water, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 23

20 parts by weight of the mixture employed in Example 3 is dissolved in a mixture consisting of 90 parts by weight of water and 10 parts by weight of the adduct of 40 moles of ethylene oxide and 1 mole of castor oil. By pouring the solution into 100,000 parts by weight of water and finely distributing it therein, an aqueous solution is obtained containing 0.02% by weight of the active ingredient.

We claim:

1. A composition for regulating plant growth, consisting essentially of a synergistic mixture of
an effective amount to regulate plant growth of
(a) N,N-dimethylpiperidinium chloride and
(b) 2-chloroethylphosphonic acid, the ratio of (a):(b) being from 1:4 to 4:1 parts by weight.

2. A composition as set forth in claim 1, containing an aqueous solution of the active ingredients.

* * * * *

UNITED STATES PATENT AND TRADEMARK OFFICE
CERTIFICATE OF CORRECTION

PATENT NO. : 4,447,255

DATED : May 8, 1984

INVENTOR(S) : Eberhard SCHOTT et al.

It is certified that error appears in the above-identified patent and that said Letters Patent is hereby corrected as shown below:

Front page, under the heading "Foreign Application Priority Data" the number should read 2755940 rather than 27559406.

Signed and Sealed this

Twenty-first Day of August 1984

[SEAL]

Attest:

GERALD J. MOSSINGHOFF

Attesting Officer

Commissioner of Patents and Trademarks